United States Patent
Ulmann

(10) Patent No.: US 9,642,853 B2
(45) Date of Patent: May 9, 2017

(54) STABLE PHARMACEUTICAL COMPOSITION CONTAINING FOLATES

(71) Applicant: APROFOL AG, Appenzell Steinegg (CH)

(72) Inventor: Martin Ulmann, Dachsen (CH)

(73) Assignee: APROFOL AG, Appenzell, Steinegg (CH)

( * ) Notice: Subject to any disclaimer, the term of this patent is extended or adjusted under 35 U.S.C. 154(b) by 39 days.

(21) Appl. No.: 14/787,980

(22) PCT Filed: Apr. 30, 2014

(86) PCT No.: PCT/EP2014/001153
§ 371 (c)(1),
(2) Date: Oct. 29, 2015

(87) PCT Pub. No.: WO2014/177274
PCT Pub. Date: Nov. 6, 2014

(65) Prior Publication Data
US 2016/0074402 A1  Mar. 17, 2016

(30) Foreign Application Priority Data
Apr. 30, 2013  (EP) .................................... 13002299

(51) Int. Cl.
| A61K 31/519 | (2006.01) |
| A61K 9/00 | (2006.01) |
| A61K 47/12 | (2006.01) |
| A61K 47/24 | (2006.01) |
| A61K 9/08 | (2006.01) |

(52) U.S. Cl.
CPC .......... *A61K 31/519* (2013.01); *A61K 9/0019* (2013.01); *A61K 9/08* (2013.01); *A61K 47/12* (2013.01); *A61K 47/24* (2013.01)

(58) Field of Classification Search
CPC ...... A61K 31/519; A61K 9/0019; A61K 9/08; A61K 47/12; A61K 47/24
USPC .......................................................... 514/249
See application file for complete search history.

(56) References Cited

U.S. PATENT DOCUMENTS

| 4,931,441 A | 6/1990 | Lawrence |
| 2007/0099866 A1 | 5/2007 | Moser |

FOREIGN PATENT DOCUMENTS

| EP | 0416232 | 3/1991 |
| EP | 1640008 | 3/2006 |
| WO | 0191734 | 12/2001 |
| WO | 2004112761 | 12/2004 |
| WO | 2010043050 | 4/2010 |

OTHER PUBLICATIONS

"Guidance for Industry," Q1A (R2) "Stability Testing of New Drug Substances and Products," Nov. 2003, pp. 1-22, U.S. Department of Health and Human Services, Food and Drug Administration.
"Particulate Matter in Injections," U. S. Pharmacopeial Convention, Revised Bulletin, Official Jul. 1, 2012, pp. 1-3.
European Search Report for European Application No. 13002298.1-1460 mailed Jul. 1, 2013.
European Search Report for European Application No. 13002299.9-1460 mailed Jul. 1, 2013.
International Search Report for International Application No. PCT/EP2014/001152 mailed Jun. 5, 2014.
International Search Report for International Application No. PCT/EP2014/001153 mailed Jun. 6, 2014.
Written Opinion of the International Searching Authority for International Application No. PCT/EP2014/001152 mailed Jun. 5, 2014.
Written Opinion of the International Searching Authority for International Application No. PCT/EP2014/001153 mailed Jun. 6, 2014.
Notice of Allowance mailed Feb. 1, 2016 in U.S. Appl. No. 14/787,984.

*Primary Examiner* — Kristin Vajda
(74) *Attorney, Agent, or Firm* — RatnerPrestia

(57) ABSTRACT

The administration of leucovorin as well as other active, reduced folates is useful as an antidote to drugs which act as folic acid antagonists and in combination chemotherapy with 5-FU. The most often used calcium salts of the folates have a low solubility in water and form almost insoluble degradation products. Therefore, aqueous solutions are unstable and precipitates result. Precipitates in injectable products present an unacceptable safety risk to patients. Stable high strength pharmaceutical aqueous compositions are formed containing calcium salts, magnesium or zinc salts of the reduced folates leucovorin, (6R,S)-tetrahydrofolic acid, (6S)-tetrahydrofolic acid, 5,10-methylene-(6R,S)-tetrahydrofolate, 5,10-methylene-(6R)-tetrahydrofolate, 5-methyl-(6R,S)-tetrahydrofolate or 5-methyl-(6S)-tetrahydrofolate and one or more of the compounds sodium gluconate, potassium gluconate, glycerophosphate disodium salt or glycerophosphate dipotassium salt.

20 Claims, No Drawings

STABLE PHARMACEUTICAL COMPOSITION CONTAINING FOLATES

CROSS-REFERENCE TO RELATED APPLICATIONS

This application is the national phase of International application PCT/EP2014/001153, filed Apr. 30, 2014, which claims priority from European application 13002299.9, filed Apr. 30, 2013. The entire disclosures of each of these applications are incorporated herein by reference for all purposes.

FIELD OF THE INVENTION

This invention relates to stable high strength pharmaceutical aqueous compositions containing folates.

DISCUSSION OF THE RELATED ART

Folates include compounds like leucovorin, levoleucovorin, (6R,S)-tetrahydrofolate, (6S)-tetrahydrofolate, 5,10-methylene-(6R,S)-tetrahydrofolate, 5,10-methylene-(6R)-tetrahydrofolate, 5-methyl-(6R,S)-tetrahydrofolate or 5-methyl-(6S)-tetrahydrofolate. Leucovorin is also known as folinic acid. Leucovorin salts, in particular leucovorin calcium, are drug substances and are a mixture of the diastereoisomers 5-formyl-(6R)-tetrahydrofolate (unnatural form) and 5-formyl-(6S)-tetrahydrofolate (natural form).

The administration of leucovorin and levoleucovorin as well as other active, reduced folates are useful as an antidote to drugs which act as folic acid antagonists and as dihydrofolate reductase inhibitors. Leucovorin or levoleucovorin are used as well in combination chemotherapy with 5-FU in the treatment of patients with e.g. metastatic colorectal cancer. Oral applications of 5-methyl-tetrahydrofolate and other reduced folates are e.g. used for the treatment of folate deficiency and cardiovascular diseases. In cancer chemotherapy typically leucovorin and levoleucovorin are administered intravenously in 10 mg folate per ml aqueous solution. Stability of these aqueous solutions is limited due to oxidative degradation. More importantly, folates and specifically their calcium salts have a low solubility in water and tend to form supersaturated solutions which are likely to form precipitates during storage. The typical strength in pharmaceutical formulations of leucovorin of 10 mg per ml (calculated as folinic acid) is well above the true solubility which is only 3 mg per ml (refrigerator: 2 to 8° C.). Therefore, commercially available aqueous solutions are unstable and tend to form precipitates during handling and storage. The appearance of such precipitates in drug products intended for intravenous administration constitutes "Particulate Matter", a critical quality defect and a significant risk for patients resulting in a recall of the affected drug products. Oxidative degradation of reduced folate is minimized if the initial solution is freeze-dried under nitrogen blanket and packaged in vials as a lyophilized powder. The product is reconstituted before use with a diluent (e.g. water for injection, 0.9% sodium chloride or 5% dextrose solution). However, limited solubility and the tendency to form precipitates remains an issue, for the "ready-to-use solution" as well as the reconstituted "lyophilized powder" form. In view of these stability issues, many of the injectable leucovorin and levoleucovorin containing drug products are used as reconstituted solutions made from "lyophilized powder". There are "ready-to-use" solutions on the market, which require a strict cold chain control during the entire distribution cycle (e.g. transport, warehouse, storage). The shelf life of the drug products is directly related to the degree of oxidative degradation of the folates, and to precipitation of less soluble degradation products. The limited aqueous solubility and possibility of precipitation dictates the limited concentration of the drug substance in the formulation and reconstituted solution. The principle reasons for the formation of particulate matter are: the crystallization of the drug substance (e.g. leucovorin) in the supersaturated solution, and the degradation of the drug substance forming less soluble compounds which precipitate, both resulting in particulate matter.

US 2007/0099866 proposes stable pharmaceutical compositions of 5,10-methylene-tetrahydrofolate with citrate formulated in a pH range between 7.5 and 10.5. The formulations are particularly suitable for producing lyophilization solutions and lyophilizates or dry powders and dry mixtures. The lyophilizates must be reconstituted by adding suitable diluents to prepare for intravenous administration. An aqueous preparation for injection is disclosed in EP 1 640 008 consisting of 5-formyl-(6S)-tetrahydrofolic acid with a basification material or a buffer agent and an antioxidant, for example ascorbic acid. U.S. Pat. No. 4,931,441 discloses an aqueous leucovorin calcium solution in the amount of 6.35 mg per ml of solution (5 mg per ml folinic acid). The low concentration of the solution reduces the benefit of the medication during administration. A stable, injectable aqueous composition comprising a salt of folic acid or leucovorin is described in EP 0 416 232. The compound benzyl alcohol is required to preserve and stabilize the composition.

For therapeutic use such pharmaceutical compositions comprise a therapeutically effective amount sufficient for the treatment of patients. As indicated herein, it is important in the preparation of aqueous injectable solutions of leucovorin as well as of other reduced folates that these drug products are made available to the patient in a stable high strength form without the risk of particulate matter formation. According to the instant invention, compositions as defined in the independent claim 1 have been developed to meet such requirements. Preferred embodiments are subject to the dependent claims.

The term "drug product" as used herein means a finished dosage form, for example, tablet, capsule, or solution, that contains a drug substance, generally, but not necessarily, in association with one or more other ingredients.

The term "drug substance" or "active pharmaceutical ingredient" (API) as used herein means an active ingredient that is intended to furnish pharmacological activity or other direct effect in the diagnosis, cure, mitigation, treatment, or prevention of disease or to affect the structure or any function of the human body.

The term "stable" as used herein means that the solution comprising the reduced folates does not form any precipitates and/or crystals over a prolonged period of time, that is, over a period of time of e.g., three years. Stability thus refers to the stability of the solution to remain free of precipitates and particulate matter over the entire period of their shelf live. Further details on the stability of drug products are found in "Guidance for Industry", Q1A (R2) "Stability Testing of New Drug Substances and Products" (November 2003), section 2.2, in particular 2.2.5 "Specification" and 2.2.7 General Case. For the determination of particulate matter a Microscopic Particle Count Test as described in "Particulate Matter in Injections", United States Pharmacopeial Convention, Revision Bulletin, Official Jul. 1, 2012 may be used.

The term "high strength" as used herein refers to solutions comprising at least 7 mg/ml of reduced folates (calculated as free acid).

SUMMARY OF THE INVENTION

Pharmaceutical aqueous compositions according to the instant invention comprise a calcium salt, a magnesium salt or a zinc salt of leucovorin, levoleucovorin, (6R,S)-tetrahydrofolic acid, (6S)-tetrahydrofolic acid, 5,10-methylene-(6R,S)-tetrahydrofolate, 5,10-methylene-(6R)-tetrahydrofolate, 5-methyl-(6R,S)-tetrahydrofolate or 5-methyl-(6S)-tetrahydrofolate and one or more of the compounds sodium gluconate, potassium gluconate, magnesium gluconate, sodium lactate, potassium lactate, magnesium lactate, glycerophosphate disodium salt, glycerophosphate dipotassium salt or glycerophosphate magnesium salt. The compositions optionally comprise a pharmaceutically acceptable buffer compound and/or a pharmaceutically acceptable antioxidant compound.

DETAILED DESCRIPTION OF CERTAIN EMBODIMENTS OF THE INVENTION

The most preferred folates are the calcium salt, a magnesium salt or a zinc salt of leucovorin, 5-methyl-(6R,S)-tetrahydrofolate or 5-methyl-(6S)-tetrahydrofolate. Preferred folates are the calcium salt, a magnesium salt or a zinc salt of 5,10-methylene-(6R,S)-tetrahydrofolate or 5,10-methylene-(6R)-tetrahydrofolate, (6R,S)-tetrahydrofolic acid, (6S)-tetrahydrofolic acid. The least preferred folate is a calcium salt, a magnesium salt or a zinc salt of levoleucovorin. The most preferred compounds are sodium gluconate, potassium gluconate, glycerophosphate disodium salt and glycerophosphate dipotassium salt. Preferred compounds are magnesium salts of gluconate and glycerophophate. Least preferred compounds are the sodium salt, the potassium salt and the magnesium salt of lactate.

In a preferred embodiment the composition according to the present invention comprises a buffer compound selected from the group consisting of trometamol (tris(hydroxymethyl)aminomethane) and HEPES (2-[4-(2-hydroxyethyl) piperazine]ethanesulfonic acid). Trometamol is the preferred buffer compound. Buffering the pharmaceutical aqueous compositions according to the present invention in the preferred range of pH 7.4 to pH 8.1 significantly stabilizes the aqueous composition and greatly reduces the formation of particulate matter.

In another preferred embodiment the composition comprises the buffer compound in a concentration range of 5 to 50 mM, preferably in a concentration range of 10 to 25 mM.

In a further preferred embodiment the composition comprises an antioxidant compound selected from the group of thioglycerol, dithiothreitol (DTT) and cystein. The most preferred antioxidant compound is thioglycerol while cystein is the least preferred antioxidant compound. The preferred amount of the antioxidant compound is in the range of 0.1% to 1.0% (w/v), more preferably in the range of 0.3% to 0.8% (w/v), most preferably in the range of 0.4% to 0.6% (w/v).

The amount of thioglycerol in the pharmaceutical aqueous composition is in the range of 0.1% to 1.0% (w/v). Preferably the amount of thioglycerol is in the range of 0.3% to 0.8% (w/v), more preferably in the range of 0.4% to 0.6% (w/v).

The compositions according to the instant invention are aqueous compositions comprising folate salts as disclosed above. The aqueous compositions remain stable for prolonged periods of time under refrigerated or room temperature storage conditions. Even after prolonged periods, no precipitation or crystallization is observed. Typical storage periods, at room temperatures of 15° to 25° C. or refrigerated at temperatures of 2° to 8° C. may extend for tests by way of example over 7, 15, 30, 60 or 120 days and in practice may last up to the end of the shelf life, for instance 12, 24 or 36 months. Aqueous solutions can be filled in containers, freeze-dried (lyophilized) to a powder and stored. The powder can be reconstituted with a diluent to a set concentration for administration. Or, aqueous solutions can be produced in a "ready to use" concentration and filled in containers, e.g. vials or ampoules. Drug products in the final form can be administered either intramuscularly or intravenously. The composition may or may not contain additional excipients. Preferably the compositions are free of compounds such as benzyl alcohol. Excipients such as mannitol for acceptable cake formation during the freeze-drying process, or sodium chloride and dextrose to adjust for osmolarity may be added to the compositions. The pH of the solutions is typically in the range of 6.5 to 8.5, preferably in the range of 7.4 to 8.1, and can be adjusted during drug product manufacturing with e.g. small amount of hydrochloric acid or sodium hydroxide. The solution may further contain a buffer and/or an antioxidant to prevent oxidative degradation of the folates.

In a composition at least one or a mixture of 2, 3 or more, practically one of the compounds calcium salt, magnesium or zinc salt of leucovorin, levoleucovorin, (6R,S)-tetrahydrofolic acid, (6S)-tetrahydrofolic acid, 5,10-methylene-(6R,S)-tetrahydrofolate, 5,10-methylene-(6R)-tetrahydrofolate, 5-methyl-(6R,S)-tetrahydrofolate or 5-methyl-(6S)-tetrahydrofolate can be used.

Pharmaceutical aqueous compositions according to the present invention remain surprisingly stable for a prolonged period of time in terms of particulate matter from the drug substance. The preferred combination of salts of gluconate, lactate or glycerophosphate with a buffer compound and/or an antioxidant compound further improves the solubility of the reduced folates and also stabilizes the reduced folates in aqueous compositions thus almost eliminating the risk of particulate matter caused by degradation products.

In a composition one, preferably one or more, for example in a mixture of 2, 3 or more, of the compounds sodium gluconate, potassium gluconate, magnesium gluconate, sodium lactate, potassium lactate, magnesium lactate, glycerophosphate disodium salt, glycerophosphate dipotassium salt, or glycerophosphate magnesium salt can be used. Preferred compositions according to the instant invention comprise one or more of the compounds sodium gluconate, potassium gluconate, sodium lactate, potassium lactate, glycerophosphate dipotassium salt or glycerophosphate disodium salt.

Regarding the amounts of the compounds in the compositions the following ratios are preferred. The compositions preferably contain for one mole of the calcium salts, magnesium salts or zinc salts of leucovorin, levoleucovorin, (6R,S)-tetrahydrofolic acid, (6S)-tetrahydrofolic acid, 5,10-methylene-(6R,S)-tetrahydrofolate, 5,10-methylene-(6R)-tetrahydrofolate, 5-methyl-(6R,S)-tetrahydrofolate, 5-methyl-(6S)-tetrahydrofolate 0.8 to 10.0 moles, advantageously 1.0 to 8.0 moles, of sodium gluconate, potassium gluconate, sodium lactate or potassium lactate. In another preferred embodiment the compositions preferably comprise for one mole of the calcium salts, magnesium salts or zinc salts of leucovorin, levoleucovorin, (6R,S)-tetrahydrofolic acid, (6S)-tetrahydrofolic acid, 5,10-methylene-(6R,S)-tetrahydrofolate, 5,10-methylene-(6R)-tetrahydrofolate, 5-methyl-(6R,S)-tetrahydrofolate or 5-methyl-(6S)-tetrahydrofolate 2.0 to 10.0 moles, advantageously 2.0 to 8.0 moles, of sodium gluconate, potassium gluconate, sodium lactate or potassium lactate.

Other compositions comprise preferably for one mole of the calcium salts, magnesium salts or zinc salts of leucovorin, levoleucovorin, (6R,S)-tetrahydrofolic acid, (6S)-tetrahydrofolic acid, 5,10-methylene-(6R,S)-tetrahydrofolate, 5,10-methylene-(6R)-tetrahydrofolate, 5-methyl-(6R,S)-tetrahydrofolate or 5-methyl-(6S)-tetrahydrofolate 0.4 to 5.0 moles, preferably 0.5 to 4.0 moles, more preferred 1.0 to 2.5, of magnesium gluconate, magnesium lactate, glycerophosphate disodium salt, glycerophosphate dipotassium salt or glycerophosphate magnesium salt. Such a composition may comprise for one mole of said salt a minimum of 0.4, preferred of 0.5 moles, and a maximum of 5.0 moles, preferably of 4.0 moles, of magnesium gluconate, magnesium lactate, glycerophosphate disodium salt, glycerophosphate dipotassium salt or glycerophosphate magnesium salt.

According to the instant invention, aqueous compositions may comprise 7 to 300 mg calcium salts, magnesium salts or zinc salts of leucovorin, levoleucovorin, (6R,S)-tetrahydrofolic acid, (6S)-tetrahydrofolic acid, 5,10-methylene-(6R,S)-tetrahydrofolate, 5,10-methylene-(6R)-tetrahydrofolate, 5-methyl-(6R,S)-tetrahydrofolate or 5-methyl-(6S)-tetrahydrofolate in 1 ml water (calculated as the free acid).

Preferred aqueous compositions according to the instant invention comprise 7 to 100 mg, preferably 10 to 50 mg, calcium salts, magnesium salts or zinc salts of leucovorin, levoleucovorin, (6R,S)-tetrahydrofolic acid, (6S)-tetrahydrofolic acid, 5,10-methylene-(6R,S)-tetrahydrofolate, 5,10-methylene-(6R)-tetrahydrofolate, 5-methyl-(6R,S)-tetrahydrofolate or 5-methyl-(6S)-tetrahydrofolate in 1 ml water (calculated as the free acid). In other words, such compositions may contain for example a minimum of 7 mg and preferably 10 mg, and a maximum for example of 300 mg, preferably of 100 mg, advantageously of 50 mg, calcium salts, magnesium salts or zinc salts of leucovorin, levoleucovorin, (6R,S)-tetrahydrofolic acid, (6S)-tetrahydrofolic acid, 5,10-methylene-(6R,S)-tetrahydrofolate, 5,10-methylene-(6R)-tetrahydrofolate, 5-methyl-(6R,S)-tetrahydrofolate or 5-methyl-(6S)-tetrahydrofolate in 1 ml water (calculated as the free acid).

Advantageous aqueous compositions comprise 7 to 100 mg, preferably 10 to 50 mg, calcium salts, magnesium salts or zinc salts of leucovorin, levoleucovorin, (6R,S)-tetrahydrofolic acid, (6S)-tetrahydrofolic acid, 5,10-methylene-(6R,S)-tetrahydrofolate, 5,10-methylene-(6R)-tetrahydrofolate, 5-methyl-(6R,S)-tetrahydrofolate or 5-methyl-(6S)-tetrahydrofolate in 1 ml water (calculated as the free acid) and the 0.8 to 10.0 molar, preferably 1.0 to 8.0 molar, amount of sodium gluconate, potassium gluconate, sodium lactate or potassium lactate. Accordingly such preferred compositions contain a minimum of a 0.8 molar amount, advantageously a 1.0 molar amount, and a maximum of up to a 10.0 molar amount, advantageously an 8.0 molar amount, of sodium gluconate, potassium gluconate, sodium lactate or potassium lactate.

Other stable high strength pharmaceutical aqueous compositions comprise 7 to 100 mg, preferably 10 to 50 mg, calcium salts, magnesium salts or zinc salts of leucovorin, levoleucovorin, (6R,S)-tetrahydrofolic acid, (6S)-tetrahydrofolic acid, 5,10-methylene-(6R,S)-tetrahydrofolate, 5,10-methylene-(6R)-tetrahydrofolate, 5-methyl-(6R,S)-tetrahydrofolate or 5-methyl-(6S)-tetrahydrofolate in 1 ml water (calculated as the free acid) and 0.4 to 5.0 molar, preferably 0.5 to 4.0 molar, amount of magnesium gluconate, magnesium lactate, glycerophosphate disodium salt, glycerophosphate dipotassium salt, or glycerophosphate magnesium salt. Accordingly such preferred compositions contain a minimum of a 0.4 molar amount, advantageously a 0.5 molar amount, and a maximum of up to a 5.0 molar amount, advantageously a 4.0 molar amount, of magnesium gluconate, magnesium lactate, glycerophosphate disodium salt, glycerophosphate dipotassium salt, or glycerophosphate magnesium salt.

Most preferred are stable high strength pharmaceutical aqueous compositions comprising 7 to 50 mg, preferably 10 to 25 mg per ml of the calcium salt of leucovorin (Leucovorin Calcium, calculated as the free acid) and a 2.0 to 10 molar amount of sodium gluconate.

Another convenient embodiment are stable high strength pharmaceutical aqueous compositions whereby the composition comprises 50 to 300 mg, preferably 100 to 200 mg, calcium salts, magnesium salts or zinc salts of leucovorin, levoleucovorin, (6R,S)-tetrahydrofolic acid, (6S)-tetrahydrofolic acid, 5,10-methylene-(6R,S)-tetrahydrofolate, 5,10-methylene-(6R)-tetrahydrofolate, 5-methyl-(6R,S)-tetrahydrofolate or 5-methyl-(6S)-tetrahydrofolate in 1 ml water (calculated as the free acid) and a 1.0 to 6.0 molar amount of sodium gluconate, potassium gluconate, sodium lactate, potassium lactate, glycerophosphate disodium salt or glycerophosphate dipotassium salt. Such very high concentrations can be used e.g. during drug product manufacturing. These very high strength solutions have to be reconstituted before use with a diluent, preferably an aqueous diluent.

The weights of leucovorin, levoleucovorin, (6R,S)-tetrahydrofolic acid, (6S)-tetrahydrofolic acid, 5,10-methylene-(6R,S)-tetrahydrofolate, 5,10-methylene-(6R)-tetrahydrofolate, 5-methyl-(6R,S)-tetrahydrofolate or 5-methyl-(6S)-tetrahydrofolate given above are calculated as the free acid.

The inventive compositions may or may not contain additional excipients and antioxidants, and are adjusted preferably to a pH of 6.5 to 8.5, more preferably to a pH of 7.4 to 8.1.

The pharmaceutical aqueous compositions according to the present invention may be used to manufacture a lyophilized powder.

Lyophilized powder is a dosage form intended for injection prepared by lyophilization ("freeze drying"), a process which involves the removal of water from products in the frozen state at extremely low pressures; this is intended for subsequent reconstitution with liquid to create a solution that conforms in all respects to the requirements for injections. While lyophilized powders made of pharmaceutical aqueous compositions comprising folates according to the present invention may be stored at room temperature, the "ready to use" pharmaceutical aqueous solutions are preferably stored at a refrigerator at 2° C. to 8° C.

The instant invention is illustrated further but not limited by the examples.

Examples 1 to 21

The following method is used for the preparation of the examples 1 to 21 listed in Table 1, 2 and 3.

(x) mg of the calcium salt of leucovorin are dissolved at temperatures of about 20° C. in 10 ml of solvent containing (y) mg of the excipient. The amount of the excipient is first dissolved in 10 ml purified water. Depending on the conditions, the temperature is increased to about 40° C. to obtain a clear solution. The clear solution is filtered with a 0.45 μm filter and divided in two parts. One part is stored in the refrigerator at 2° C. to 8° C., the other one kept at room temperature at 15° C. to 25° C. The storage conditions and storage times applied are disclosed in columns "storage, room temperature" and "storage refrigerator". At the end of the test period the samples are checked and rated. The rating "clear" is used, if no precipitation is visible in the fluid of the test sample, "cryst." is used in case a precipitate in the fluid or at the bottom of the test vial is visible.

In an additional test, samples are stored for 7 days and are seeded afterwards with a few crystals of the calcium salt of leucovorin. The crystallization characteristics are observed 24 hours after seeding. In column "storage, refrigerator, seeding" the results are recorded. In some of the examples the seeding crystals dissolve and disappear. If the seeding crystals dissolve and disappear, the rating is "clear". In other examples the seeding crystals remain but do not cause any precipitation or crystallization. A rating "seed" means, the seeding crystals remain, but did not initiate precipitation.

In Table 1, 2, 3 and 4 "Na-Glc" indicates sodium gluconate, "Na-Lac" indicates sodium lactate, "K-Glc" indicates potassium gluconate and "Gly" indicates glycerophosphate disodium salt.

Table 2 shows the examples 1 to 21 whereby the storage period at room temperature has been extended to two months. The results demonstrate that none of the examples shows any precipitation or particulate matter.

Table 3 shows the examples 1 to 21 whereby the storage period at 2° C. to 8° C. temperature (refrigerator) has been extended to ten months. The results after a storage period of ten months in the refrigerator correspond to results of the stress test which has been performed by seeding the samples with a few crystals of calcium leucovorin and assessing their status after 24 h as described above.

Additional Examples 22 to 25

Example 22

4.0 g of leucovorin calcium (6.7 mmol) are suspended in 100 ml water. The slurry is heated up to about 40° C. to obtain a clear solution. 1.0 g of zinc acetate dihydrate (4.6 mmol) in 10 ml water is slowly added. A precipitate is formed immediately. After one day the precipitate is separated from the mother liquor. Yield: 2.5 g leucovorin zinc (4.0 mmol), almost insoluble in water. 0.4 g of the above leucovorin zinc is added to a solution containing 1.0 g sodium gluconate in 30 ml water. After 15 minutes a clear solution is obtained forming no precipitate over 10 days at room temperature.

Example 23

400 mg of the calcium salt of 5-methyl-(6R,S)-tetrahydrofolic acid are dissolved at a temperature of about 20° C. in 30 ml of solvent containing 1.44 g of sodium gluconate. The amount of the excipient is first dissolved in 30 ml purified water. The temperature is increased to about 40° C. to obtain a clear solution. The clear solution is filtered with a 0.45 μm filter and divided in two parts. One part is stored in the refrigerator at 2° C. to 8° C., the other one is kept at room temperature at 15° C. to 25° C. No precipitation or crystallization occurs after 7 days, neither at room temperature nor in the refrigerator.

Example 24

1.00 g of the calcium salt of 5-methyl-(6R,S)-tetrahydrofolic acid are dissolved at a temperature of about 20° C. in 30 ml of solvent containing 2.88 g of sodium gluconate. The amount of the excipient is first dissolved in 30 ml purified water. The temperature is increased to about 40° C. to obtain a clear solution. The clear solution is filtered with a 0.45 μm filter and divided in two parts. One part is stored in the refrigerator at 2° C. to 8° C., the other one is kept at room temperature at 15° C. to 25° C. No precipitation or crystallization occurs after 7 days, neither at room temperature nor in the refrigerator.

Example 25

4.00 g of leucovorin calcium are dissolved at a temperature of about 20° C. in 30 ml of solvent containing 5.76 g of sodium gluconate. The amount of the excipient is first dissolved in 30 ml purified water. The temperature is increased to about 40° C. to obtain a clear solution. The clear solution is filtered with a 0.45 μm filter and divided in two parts. One part is stored in the refrigerator at 2° C. to 8° C., the other one kept at room temperature at 15° C. to 25° C. No precipitation or crystallization occurs after 7 days, neither at room temperature nor in the refrigerator.

Examples 26 to 33

The following method is used for the preparation of the examples 26 to 33 listed in Table 4. In Table 4 "Thio" indicates thioglycerol and "DTT" indicates dithiothreitol.

(x) mg/ml of the calcium salt of leucovorin are dissolved at temperatures of about 20° C. in 40 ml of solvent containing (y) molar amount of sodium gluconate. The excipient is first dissolved in 40 ml purified water. Optionally the buffer compound and/or the antioxidant in the given concentration is added. Depending on the conditions, the temperature is increased to about 40° C. to obtain a clear solution. The pH is adjusted to a range in between 7.4 to 8.1 with hydrochloric acid or sodium hydroxide. The clear solution is filtered with a 0.45 μm filter and divided in different parts. One part was stored in the refrigerator at 4° C., another one kept at room temperature at 25° C. respectively at 40° C. (stress test). The solutions at 40° C. (stress test) are analysed with HPLC after 60 days.

Table 4 shows the results for examples 26 to 33. Examples 26 to 33 represent compositions comprising leucovorin, with or without a buffer compound and with or without an antioxidant compound. The compositions comprise the compounds as indicated in table 4. The samples were stored for 60 days at 40° C. (stress test). After the storage period the samples are analysed to measure the amount of leucovorin. Samples comprising leucovorin alone were used as comparison. The measurement was performed according to the method described in US Pharmacopeia 35, monograph leucovorin calcium tablets pages 3651-3652. In brief, the samples were analysed by HPLC on RP-C18 column (4.6 mm×150 mm). The mobile phase was 0.005M tetrabutylammoniumphosphate in water and methanol (80:20) at a flow rate of 2 ml/min. Detection was done by UV measurement at a wavelength of 254 nm. The amount of leucovorin is indicated as percentage of the initial amount. The quantitative assay was calculated according to USP 35 (% w/v, external standard).

TABLE 1

| No. | Amount Leucovorin ("L") (x) mg per 10 ml | Amount Leucovorin ("L") in mg per ml, based on the free acid | Excipient ("E") Name | Excipient ("E") (y) mg per 10 ml | Ratio mol L/mol E | Storage room temp. 15 days | Storage refrigerator 7 days | Storage refrigerator seeding |
|---|---|---|---|---|---|---|---|---|
| 1 | 133 | 10 | Na-Glc | 96 | 1 to 2 | clear | clear | cryst. |
| 2 | 133 | 10 | Na-Lac | 82 | 1 to 2 | clear | clear | cryst. |
| 3 | 133 | 10 | Gly | 100 | 1 to 2 | clear | clear | cryst. |
| 4 | 266 | 20 | Na-Glc | 96 | 1 to 1 | clear | clear | cryst. |
| 5 | 266 | 20 | Na-Lac | 82 | 1 to 1 | clear | clear | cryst. |
| 6 | 266 | 20 | Gly | 100 | 1 to 1 | clear | clear | cryst. |
| 7 | 133 | 10 | Na-Glc | 50 | 1 to 1 | clear | clear | cryst. |
| 8 | 133 | 10 | Na-Glc | 50 | 1 to 2 | clear | clear | cryst. |
| 9 | 333 | 25 | Na-Glc | 240 | 1 to 2 | clear | clear | cryst. |
| 10 | 666 | 50 | Na-Glc | 960 | 1 to 4 | clear | clear | cryst. |
| 11 | 133 | 10 | Na-Glc | 480 | 1 to 10 | clear | clear | clear |
| 12 | 333 | 25 | Na-Glc | 480 | 1 to 4 | clear | clear | seed |
| 13 | 333 | 25 | Na-Lac | 410 | 1 to 4 | clear | clear | cryst. |
| 14 | 333 | 25 | Gly | 500 | 1 to 4 | clear | clear | cryst. |
| 15 | 333 | 25 | K-Glc | 520 | 1 to 4 | clear | clear | cryst. |
| 16 | 1333 | 100 | Na-Glc | 1920 | 1 to 4 | clear | clear | cryst. |
| 17 | 333 | 25 | Na-Lac | 820 | 1 to 8 | clear | clear | seed |
| 18 | 333 | 25 | Gly | 1000 | 1 to 8 | clear | clear | seed |
| 19 | 333 | 25 | K-Glc | 1040 | 1 to 8 | clear | clear | clear |
| 20 | 133 | 10 | Na-Glc | 200 | 1 to 4 | clear | clear | seed |
| 21 | 333 | 25 | Na-Glc | 960 | 1 to 8 | clear | clear | clear |

TABLE 2

| No. | Amount Leucovorin ("L") (x) mg per 10 ml | Amount Leucovorin ("L") in mg per ml, based on the free acid | Excipient ("E") Name | Excipient ("E") (y) mg per 10 ml | Ratio mol L/mol E | Storage room temp. 15 days | Storage room temp. 2 months |
|---|---|---|---|---|---|---|---|
| 1 | 133 | 10 | Na-Glc | 96 | 1 to 2 | clear | clear |
| 2 | 133 | 10 | Na-Lac | 82 | 1 to 2 | clear | clear |
| 3 | 133 | 10 | Gly | 100 | 1 to 2 | clear | clear |
| 4 | 266 | 20 | Na-Glc | 96 | 1 to 1 | clear | clear |
| 5 | 266 | 20 | Na-Lac | 82 | 1 to 1 | clear | clear |
| 6 | 266 | 20 | Gly | 100 | 1 to 1 | clear | clear |
| 7 | 133 | 10 | Na-Glc | 50 | 1 to 1 | clear | clear |
| 8 | 133 | 10 | Na-Glc | 50 | 1 to 2 | clear | clear |
| 9 | 333 | 25 | Na-Glc | 240 | 1 to 2 | clear | clear |
| 10 | 666 | 50 | Na-Glc | 960 | 1 to 4 | clear | clear |
| 11 | 133 | 10 | Na-Glc | 480 | 1 to 10 | clear | clear |
| 12 | 333 | 25 | Na-Glc | 480 | 1 to 4 | clear | clear |
| 13 | 333 | 25 | Na-Lac | 410 | 1 to 4 | clear | clear |
| 14 | 333 | 25 | Gly | 500 | 1 to 4 | clear | clear |
| 15 | 333 | 25 | K-Glc | 520 | 1 to 4 | clear | clear |
| 16 | 1333 | 100 | Na-Glc | 1920 | 1 to 4 | clear | clear |
| 17 | 333 | 25 | Na-Lac | 820 | 1 to 8 | clear | clear |
| 18 | 333 | 25 | Gly | 1000 | 1 to 8 | clear | clear |
| 19 | 333 | 25 | K-Glc | 1040 | 1 to 8 | clear | clear |
| 20 | 133 | 10 | Na-Glc | 200 | 1 to 4 | clear | clear |
| 21 | 333 | 25 | Na-Glc | 960 | 1 to 8 | clear | clear |

TABLE 3

| No. | Amount Leucovorin ("L") (x) mg per 10 ml | Amount Leucovorin ("L") in mg per ml, based on the free acid | Excipient ("E") Name | Excipient ("E") (y) mg per 10 ml | Ratio mol L/mol E | Storage refrigerator 7 days | Storage refrigerator 10 months | Storage refrigerator seeding |
|---|---|---|---|---|---|---|---|---|
| 1 | 133 | 10 | Na-Glc | 96 | 1 to 2 | clear | cryst. | cryst. |
| 2 | 133 | 10 | Na-Lac | 82 | 1 to 2 | clear | cryst. | cryst. |
| 3 | 133 | 10 | Gly | 100 | 1 to 2 | clear | cryst. | cryst. |
| 4 | 266 | 20 | Na-Glc | 96 | 1 to 1 | clear | cryst. | cryst. |
| 5 | 266 | 20 | Na-Lac | 82 | 1 to 1 | clear | cryst. | cryst. |
| 6 | 266 | 20 | Gly | 100 | 1 to 1 | clear | cryst. | cryst. |
| 7 | 133 | 10 | Na-Glc | 50 | 1 to 1 | clear | cryst. | cryst. |
| 8 | 133 | 10 | Na-Glc | 50 | 1 to 2 | clear | cryst. | cryst. |
| 9 | 333 | 25 | Na-Glc | 240 | 1 to 2 | clear | cryst. | cryst. |
| 10 | 666 | 50 | Na-Glc | 960 | 1 to 4 | clear | cryst. | cryst. |
| 11 | 133 | 10 | Na-Glc | 480 | 1 to 10 | clear | clear | clear |
| 12 | 333 | 25 | Na-Glc | 480 | 1 to 4 | clear | clear | seed |
| 13 | 333 | 25 | Na-Lac | 410 | 1 to 4 | clear | cryst. | cryst. |
| 14 | 333 | 25 | Gly | 500 | 1 to 4 | clear | cryst. | cryst. |
| 15 | 333 | 25 | K-Glc | 520 | 1 to 4 | clear | cryst. | cryst. |
| 16 | 1333 | 100 | Na-Glc | 1920 | 1 to 4 | clear | cryst. | cryst. |
| 17 | 333 | 25 | Na-Lac | 820 | 1 to 8 | clear | clear | seed |
| 18 | 333 | 25 | Gly | 1000 | 1 to 8 | clear | clear | seed |
| 19 | 333 | 25 | K-Glc | 1040 | 1 to 8 | clear | clear | clear |
| 20 | 133 | 10 | Na-Glc | 200 | 1 to 4 | clear | clear | seed |
| 21 | 333 | 25 | Na-Glc | 960 | 1 to 8 | clear | clear | clear |

TABLE 4

Stability of Leucovorin Solutions after 60 days at 40° C.

| | Concentration mg/mL as folinic acid | Excipients Na-Glc molar ratio | Buffer Trometamol/ HEPES* mg/mL | Antioxidant | Assay % |
|---|---|---|---|---|---|
| 26 | 10 | without | 0 | 0 | 75.5 |
| 27 | 10 | 1:2 | 5 | 0 | 83.6 |
| 28 | 10 | 1:2 | 3 | 0.5% Thio | 88.6 |
| 29 | 10 | 1:2 | 3* | 0 | 82.3 |
| 30 | 10 | 1:2 | 3* | 0.5% Thio | 85.6 |
| 31 | 10 | 1:2 | 3 | 0.5% DTT | 94.5 |
| 32 | 10 | 1:2 | 3 | 0.5% Cystein | 90.5 |
| 33 | 20 | 1:1.6 | 3 | 0.5% Thio | 83.3 |

The invention claimed is:

1. A pharmaceutical aqueous composition containing folates wherein the composition comprises a calcium salt, magnesium salt or zinc salt of leucovorin, (6R,S)-tetrahydrofolic acid, (6S)-tetrahydrofolic acid, 5,10-methylene-(6R,S)-tetrahydrofolate, 5,10-methylene-(6R)-tetrahydrofolate, 5-methyl-(6R,S)-tetrahydrofolate or 5-methyl-(6S)-tetrahydrofolate, optionally a pharmaceutically acceptable buffer compound, optionally a pharmaceutically acceptable antioxidant compound and one or more of the compounds sodium gluconate, potassium gluconate, glycerophosphate disodium salt or glycerophosphate dipotassium salt.

2. The pharmaceutical aqueous composition according to claim 1, wherein the composition comprises a pharmaceutically acceptable buffer compound and the buffer compound is selected from the group consisting of trometamol and HEPES.

3. The pharmaceutical aqueous composition according to claim 2, wherein the composition comprises the buffer compound in a concentration range of 5 to 50 mM.

4. The pharmaceutical aqueous composition according to claim 1, wherein the composition comprises a pharmaceutically acceptable antioxidant compound and the antioxidant compound is selected from the group consisting of thioglycerol, dithiothreitol and cystein in the range of 0.1% to 1.0% (w/v).

5. The pharmaceutical aqueous composition according to claim 1, wherein the composition comprises a calcium salt of leucovorin, (6R,S)-tetrahydrofolic acid, (6S)-tetrahydrofolic acid, 5,10-methylene-(6R,S)-tetrahydrofolate, 5,10-methylene-(6R)-tetrahydrofolate, 5-methyl-(6R,S)-tetrahydrofolate or 5-methyl-(6S)-tetrahydrofolate.

6. The pharmaceutical aqueous composition according to claim 1, wherein the composition contains for one mole of the calcium salt, magnesium salt or zinc salt of leucovorin, (6R,S)-tetrahydrofolic acid, (6S)-tetrahydrofolic acid, 5,10-methylene-(6R,S)-tetrahydrofolate, 5,10-methylene-(6R)-tetrahydrofolate, 5-methyl-(6R,S)-tetrahydrofolate or 5-methyl-(6S)-tetrahydrofolate 0.8 to 10 moles of sodium gluconate or potassium gluconate.

7. The pharmaceutical aqueous composition according to claim 1, wherein the composition contains for one mole of the calcium salt, magnesium salt or zinc salt of leucovorin, (6R,S)-tetrahydrofolic acid, (6S)-tetrahydrofolic acid, 5,10-methylene-(6R,S)-tetrahydrofolate, 5,10-methylene-(6R)-tetrahydrofolate, 5-methyl-(6R,S)-tetrahydrofolate or 5-methyl-(6S)-tetrahydrofolate 2.0 to 10 moles of sodium gluconate or potassium gluconate.

8. The pharmaceutical aqueous composition according to claim 1, wherein the composition contains for one mole of the calcium salt, magnesium salt or zinc salt of leucovorin, (6R,S)-tetrahydrofolic acid, (6S)-tetrahydrofolic acid, 5,10-methylene-(6R,S)-tetrahydrofolate, 5,10-methylene-(6R)-tetrahydrofolate, 5-methyl-(6R,S)-tetrahydrofolate or 5-methyl-(6S)-tetrahydrofolate 0.4 to 5.0 moles of glycerophosphate disodium salt or glycerophosphate dipotassium salt.

9. The pharmaceutical aqueous composition according to claim 1, wherein the composition comprises 7 to 300 mg calcium salt, magnesium salt or zinc salt of leucovorin, (6R,S)-tetrahydrofolic acid, (6S)-tetrahydrofolic acid, 5,10-methylene-(6R,S)-tetrahydrofolate, 5,10-methylene-(6R)- tetrahydrofolate, 5-methyl-(6R,S)-tetrahydrofolate or 5-methyl-(6S)-tetrahydrofolate in 1 ml water (calculated as the free acid).

10. The pharmaceutical aqueous composition according to claim 1, wherein the composition comprises 7 to 100 mg calcium salt, magnesium salt or zinc salt of leucovorin, (6R,S)-tetrahydrofolic acid, (6S)-tetrahydrofolic acid, 5,10-methylene-(6R,S)-tetrahydrofolate, 5,10-methylene-(6R)-tetrahydrofolate, 5-methyl-(6R,S)-tetrahydrofolate or 5-methyl-(6S)-tetrahydrofolate in 1 ml water (calculated as the free acid) and 0.8 to 10.0 molar amount of sodium gluconate or potassium gluconate.

11. The pharmaceutical aqueous composition according to claim 1, wherein the composition comprises 7 to 100 mg calcium salt, magnesium salt or zinc salt of leucovorin, (6R,S)-tetrahydrofolic acid, (6S)-tetrahydrofolic acid, 5,10-methylene-(6R,S)-tetrahydrofolate, 5,10-methylene-(6R)-tetrahydrofolate, 5-methyl-(6R,S)-tetrahydrofolate or 5-methyl-(6S)-tetrahydrofolate in 1 ml water (calculated as the free acid) and 0.4 to 5.0 molar amount of glycerophosphate disodium salt or glycerophosphate dipotassium salt.

12. The pharmaceutical aqueous composition according to claim 1, wherein the composition comprises 50 to 300 mg calcium salt, magnesium salt or zinc salt of leucovorin, (6R,S)-tetrahydrofolic acid, (6S)-tetrahydrofolic acid, 5,10-methylene-(6R,S)-tetrahydrofolate, 5,10-methylene-(6R)-tetrahydrofolate, 5-methyl-(6R,S)-tetrahydrofolate or 5-methyl-(6S)-tetrahydrofolate in 1 ml water (calculated as the free acid) and 1.0 to 6.0 molar amount of sodium gluconate, potassium gluconate, glycerophosphate disodium salt or glycerophosphate dipotassium salt.

13. The pharmaceutical aqueous composition according to claim 1, wherein the composition comprises 7 to 50 mg per ml of the calcium salt of leucovorin (Leucovorin Calcium, calculated as the free folinic acid) and 2.0 to 8.0 moles of sodium gluconate for one mole of the calcium salt of leucovorin.

14. A method for manufacturing a lyophilized powder, comprising lyophilizing the pharmaceutical aqueous composition of claim 1.

15. The pharmaceutical aqueous composition according to claim 2, wherein the composition comprises the buffer compound in a concentration range of 10 to 25 mM.

16. The pharmaceutical aqueous composition according to claim 1, wherein the composition comprises a pharmaceutically acceptable antioxidant compound and the antioxidant compound is selected from the group consisting of thioglycerol, dithiothreitol and cystein in the range of 0.3% to 0.8% (w/v).

17. The pharmaceutical aqueous composition according to claim 1, wherein the composition contains for one mole of the calcium salt, magnesium salt or zinc salt of leucovorin, (6R,S)-tetrahydrofolic acid, (6S)-tetrahydrofolic acid, 5,10-methylene-(6R,S)-tetrahydrofolate, 5,10-methylene-(6R)-tetrahydrofolate, 5-methyl-(6R,S)-tetrahydrofolate or 5-methyl-(6S)-tetrahydrofolate 1.0 to 8.0 moles of sodium gluconate or potassium gluconate.

18. The pharmaceutical aqueous composition according to claim 1, wherein the composition contains for one mole of the calcium salt, magnesium salt or zinc salt of leucovorin, (6R,S)-tetrahydrofolic acid, (6S)-tetrahydrofolic acid, 5,10-methylene-(6R,S)-tetrahydrofolate, 5,10-methylene-(6R)-tetrahydrofolate, 5-methyl-(6R,S)-tetrahydrofolate or 5-methyl-(6S)-tetrahydrofolate 2.0 to 8.0 moles of sodium gluconate or potassium gluconate.

19. The pharmaceutical aqueous composition according to claim 1, wherein the composition contains for one mole of the calcium salt, magnesium salt or zinc salt of leucovorin, (6R,S)-tetrahydrofolic acid, (6S)-tetrahydrofolic acid, 5,10-methylene-(6R,S)-tetrahydrofolate, 5,10-methylene-(6R)-tetrahydrofolate, 5-methyl-(6R,S)-tetrahydrofolate or 5-methyl-(6S)-tetrahydrofolate 0.5 to 4.0 moles of glycerophosphate disodium salt or glycerophosphate dipotassium salt.

20. The pharmaceutical aqueous composition according to claim 1, wherein the composition comprises 10 to 50 mg calcium salt, magnesium salt or zinc salt of leucovorin, (6R,S)-tetrahydrofolic acid, (6S)-tetrahydrofolic acid, 5,10-methylene-(6R,S)-tetrahydrofolate, 5,10-methylene-(6R)-tetrahydrofolate, 5-methyl-(6R,S)-tetrahydrofolate or 5-methyl-(6S)-tetrahydrofolate in 1 ml water (calculated as the free acid) and 1.0 to 8.0 molar amount of sodium gluconate or potassium gluconate.

* * * * *